US012766331B2

(12) United States Patent
Schumaier

(10) Patent No.: US 12,766,331 B2
(45) Date of Patent: Oct. 20, 2026

(54) MAGNETIC EAR DEVICES FOR TREATMENT OF TINNITUS, HEARING LOSS, AND VERTIGO

(71) Applicant: Daniel R. Schumaier, Elizabethton, TN (US)

(72) Inventor: Daniel R. Schumaier, Elizabethton, TN (US)

( * ) Notice: Subject to any disclaimer, the term of this patent is extended or adjusted under 35 U.S.C. 154(b) by 0 days.

(21) Appl. No.: 18/924,241

(22) Filed: Oct. 23, 2024

(65) Prior Publication Data

US 2025/0312612 A1 Oct. 9, 2025

Related U.S. Application Data

(62) Division of application No. 18/744,603, filed on Jun. 15, 2024.

(60) Provisional application No. 63/631,465, filed on Apr. 9, 2024.

(51) Int. Cl.

| | |
|---|---|
| ***A61N 2/00*** | (2006.01) |
| ***A61N 2/02*** | (2006.01) |
| ***A61N 2/06*** | (2006.01) |

(52) U.S. Cl.

CPC ............... *A61N 2/004* (2013.01); *A61N 2/02* (2013.01); *A61N 2/06* (2013.01)

(58) Field of Classification Search

CPC . A61N 2/004; A61N 2/02; A61N 2/06; A61N 2/00; A61N 2/002; A61B 5/6815; A61B 17/1679–1771; A61B 1/00158; A61B 5/062; A61F 13/2017; A61F 11/00; A61F 11/08; A61F 11/085; A61F 11/10; A61M 2205/8287

See application file for complete search history.

(56) References Cited

U.S. PATENT DOCUMENTS

| | | | | |
|---|---|---|---|---|
| 4,865,035 A | | 9/1989 | Mori | |
| 6,398,713 B1 | * | 6/2002 | Ewing | A61N 2/06 600/9 |
| 2009/0250072 A1 | * | 10/2009 | Collins | A61F 11/08 128/864 |

(Continued)

FOREIGN PATENT DOCUMENTS

| | | | | |
|---|---|---|---|---|
| CN | 2074189 U | * | 4/1991 | |
| CN | 101626745 A | * | 1/2010 | A61F 11/08 |

(Continued)

*Primary Examiner* — Charles A Marmor, II

(74) *Attorney, Agent, or Firm* — Luedeka Neely, P.C.; Mark P. Crockett

(57) ABSTRACT

An apparatus directs a magnetic field to an inner ear of a user to improve blood flow and oxygen levels for treatment of one or all of tinnitus, sudden sensorineural hearing loss, and vertigo. The apparatus includes an outer shell having an outer profile that is custom-molded to fit one or more portions of an ear of the user. Magnetic material disposed within the outer shell. A sound tube is disposed within the outer shell and passes through the magnetic material. The sound tube has an outer opening that receives sound from outside the ear of the user and an inner opening through which the sound passes into an ear canal of the user. The magnetic material is configured to direct a negative magnetic field to the inner ear of the user when the outer shell is disposed within a portion of the user's ear.

5 Claims, 10 Drawing Sheets

(56) References Cited

U.S. PATENT DOCUMENTS

| | | | | |
|---|---|---|---|---|
| 2010/0145147 | A1 | 6/2010 | Pinsky et al. | |
| 2011/0137106 | A1 | 6/2011 | Liang et al. | |
| 2013/0092470 | A1 | 4/2013 | Johnston et al. | |
| 2013/0251161 | A1* | 9/2013 | Lott | H04R 1/1016 381/58 |
| 2015/0360030 | A1 | 12/2015 | Cartledge et al. | |
| 2018/0133497 | A1 | 5/2018 | Lee et al. | |
| 2018/0160242 | A1* | 6/2018 | Sriskandarajah | H04R 25/606 |
| 2019/0046794 | A1 | 2/2019 | Goodall et al. | |
| 2020/0000406 | A1 | 1/2020 | Saidi | |
| 2023/0031813 | A1 | 2/2023 | Leigh | |
| 2023/0224647 | A1* | 7/2023 | Saidi | H04R 25/00 600/364 |

FOREIGN PATENT DOCUMENTS

| | | | | | |
|---|---|---|---|---|---|
| CN | 205252325 | U | * | 5/2016 | |
| CN | 107714283 | A | * | 2/2018 | A61N 2/06 |
| CN | 221490410 | U | * | 8/2024 | |
| WO | 2022133459 | A1 | | 6/2022 | |
| WO | 2022268301 | A1 | | 12/2022 | |

* cited by examiner (Section A-A)

MAGNETIC EAR DEVICES FOR TREATMENT OF TINNITUS, HEARING LOSS, AND VERTIGO

FIELD

This invention relates to the treatment of health conditions using magnetic fields. More particularly, this invention relates to wearable devices that apply magnetic fields near blood vessels in the ears to improve blood flow for treatment of tinnitus, vertigo, and sudden sensorineural hearing loss.

BACKGROUND

Magnetic energy for healing dates back thousands of years. For example, a book published in China around 2000 B.C., entitled "The Yellow Emperor's Book of Internal Medicine," mentions using magnetic stones to correct health imbalances. Such stones, which contain a naturally occurring mineral called magnetite (Fe304), have been referred to as Lodestones. The ancient Greeks also knew about the healing effects of Lodestones, and Hippocrates, who is considered the Father of Medicine, talked about the healing powers of Lodestones.

Electromagnetic therapy devices are now being used to eliminate pain, improve healing of broken bones, and reverse degenerative diseases. Magnetic therapy is well accepted in such countries as Germany, Russia, China, Japan, and Australia, just to name a few. More and more American studies are confirming the value of magnetic therapy in healing, and magnetic therapy is gaining credibility in the United States.

Magnets are showing results in healing in general, as well as for cuts, broken bones, inflammation, pain, and more. It is well known that negative magnetic fields have a beneficial effect, and positive magnetic fields have a stressful effect. Research has shown that the north (negative) pole of a magnetic field increases tissue oxygenation, relieves pain, reduces swelling, and promotes tissue alkalinization. On the other hand, the south (positive) pole increases swelling, promotes tissue acidity, and decreases tissue oxygenation. Therefore, the polar direction of the magnetic field is critical for healing. Magnetic strength is another critical factor. Both the correct magnetic strength and the correct magnetic pole orientation must be applied to the affected area to be beneficial.

Research by Rongia Tal, a Temple University physicist, has demonstrated that human blood flow can be improved by subjecting it to a magnetic field. Red blood cells contain iron. "A magnetic field polarizes the red blood cells, causing them to link together to form chains, thus streamlining the movement of the blood. Since these chains are larger than the single cells, they flow down the center, reducing friction against the walls of the blood vessels." Improved blood flow brings more oxygen to a magnetized area.

It is thought that tinnitus is usually caused by an underlying condition, such as age-related hearing loss, an ear injury, or a problem with the circulatory system. For example, tinnitus can be caused by broken or damaged hair cells in the part of the ear that receives sound (cochlea), changes in how blood moves through nearby blood vessels (carotid artery), problems with the joint of the jawbone (temporomandibular joint), and problems with how the brain processes sound. Blood vessel disorders may also cause tinnitus. Conditions that affect blood vessels, such as atherosclerosis, high blood pressure, or kinked or malformed blood vessels, can cause blood to move through veins and arteries with more force. These blood flow changes can cause tinnitus or make tinnitus more noticeable.

For many people, tinnitus can be improved with treatment of the underlying cause. It has also been treated by masking the noise, thereby making tinnitus less noticeable. Research has been conducted in the use of repetitive transcranial magnetic stimulation (rTMS) to treat tinnitus. This involves delivering short magnetic pulses to the brain using an electromagnetic coil. Because preliminary trials of rTMS have yielded mixed results, researchers are studying the ideal coil placement and frequency of treatments.

Because all hearing is centered on the cochlea, the blood supply provided to the cochlea via the labyrinthine artery (internal auditory artery) is critical. Interruption of this blood flow can cause damage to the stereocilia, resulting in partial to sudden sensorineural hearing loss, tinnitus, and vertigo. Loud noises for prolonged periods of time can also cause damage to the stereocilia due to a decrease in blood flow and oxygen levels, and the inability of the cells to get rid of waste products. Also, an interruption of the blood flow to the vestibular portion of the inner ear can cause vertigo and dizziness.

Each year, more than 66,000 people in the United States experience a sudden sensorineural hearing loss (SSHL). SSHL is experienced as a sudden loss of most or all of the hearing in one ear and is thought to be caused by a sudden blockage of the blood supply to the cochlea provided by the labyrinthine artery. SSHL is generally defined as hearing loss of at least 30 decibels occurring over at least three consecutive audiometric frequencies and lasting at least three days. Those experiencing SSHL may also experience tinnitus, dizziness or vertigo. Any pathology that results in vascular occlusion of the labyrinthine artery can result in SSHL. SSHL has also been associated with decreased oxygen tension in the perilymph, which is an extracellular fluid located within the scala tympani and scala vestibuli of the cochlea. There is also evidence that iron-deficiency anemia may increase the risk for SSHL. Studies have shown that hyperbaric oxygen therapy can increase oxygen tension in the perilymph and restore hearing in a significant number of patients with SSHL. Studies have also shown that the three most promising treatments for SSHL include corticosteroids, hyperbaric oxygen therapy, and vasodilators.

Thus, the vascular system in the inner ear is very critical. In addition to traditional medical treatments, such as those involving corticosteroids, hyperbaric oxygen therapy, and vasodilators, a treatment option is needed to help to increase the blood supply to and blood oxygen levels in the inner ear to maximize the chance of recovery. The needed treatment option should be implemented using comfortable wearable devices that apply magnetic fields near blood vessels in the ears to improve blood flow and increase blood oxygen levels.

SUMMARY

There are three major problems that may occur with poor blood flow and/or oxygen levels in the inner ear: sudden sensorineural hearing loss, tinnitus, and vertigo (dizziness). Evidence suggests that these issues may be improved through magnetic therapy directed at the inner ear.

Electromagnetism (aka magnetism) does not relate only to iron and other metals. Almost anything can be magnetized. Magnetism occurs on an atomic level in which electrons orbit around the nucleus of the atom. These same electrons spin like the Earth, creating miniature magnetic fields with north and south poles. If all electrons spin in the same direction, magnetism results from an alignment of electrons. Magnetic field power increases as more electrons are aligned.

All magnets have two poles: a negative (north) pole and a positive (south) pole. Most permanent magnets contain one or two magnetizable metals, such as iron oxide and the rare earth metal neodymium. The strength of a magnet is measured in units of Gauss. Earth has a magnetic field that produces electromotive energy. One Gauss is equivalent to about twice the average of Earth's magnetic field. Earth's magnetic field has been dwindling over the last 500 years, which has caused a loss of Gauss strength, a deficiency which can cause medical problems such as stiffness, headaches, dizziness, and the loss of normal healing.

A negative magnetic field favorably affects cell function, hormone production, enzyme activity, to name a few. Negative magnetic fields normalize blood pH levels, reduce cellular swelling, and release molecular oxygen. It is well known that the application of a magnetic negative pole to areas of the body increases blood flow and flow of the lymph system.

With regard to magnetic treatments, evidence suggests that continuous application of low-intensity magnetic fields to blood vessels in the inner ears can improve blood flow and oxygen levels, thereby reducing tinnitus. The inner ear also has a vestibular system that uses the same fluids which may respond with improved blood flow and oxygen levels. The blood supply to the inner ears is also critical to the health of the hair cells for normal hearing. Again, magnetic therapy may improve the blood supply to the inner ear, thereby reducing the loss of these hair cells that cause sudden sensorineural hearing loss and tinnitus.

Embodiments of the invention described herein provide an apparatus for directing a magnetic field to a user's inner ear to improve blood flow and oxygen levels for treatment of one or all of tinnitus, sudden sensorineural hearing loss, and vertigo. A preferred embodiment of the apparatus comprises a headband configured to wrap around the user's head and one or more housing assemblies attached to the headband. Each housing assembly includes a base portion and a cover portion. The base portion has a pair of opposing lug portions for slidingly receiving the headband. The cover portion is configured to attach to the base portion, thereby forming a cavity between the base portion and the cover portion. Secured within the cavity is magnetic material configured such that the magnetic field it generates is directed to the inner ear of the user when the housing assembly is disposed adjacent the user's ear.

In some embodiments, the magnetic material is oriented within the housing assembly such that the north pole of the magnetic material is directed toward the user's ear, and the south pole is directed away from the user's ear.

In some embodiments, the base and cover portions of the housing assembly are oval-shaped, and the lug portions are disposed on opposing sides of the base portion in alignment with the minor axes of the oval.

In some embodiments, the base portion includes first cradle protrusions that are disposed in a circular arrangement on a central portion of the inner surface of the base portion. The magnetic material comprises one or more circular disks that are disposed between and are at least partially encircled by the first cradle protrusions. The cover portion includes second cradle protrusions extending from a central portion of the inner surface of the cover portion. The second cradle protrusions, which are also disposed in a circular arrangement, are configured to have a snap-fit engagement with the first cradle protrusions.

In some embodiments, the one or more circular disks comprise neodymium.

In some embodiments, the one or more circular magnetic disks generate a magnetic flux density ranging from about 580 Gs to about 1390 Gs.

In some embodiments, the magnetic material comprises an electromagnet.

In some embodiments, the headband is configured to position each housing assembly over the corresponding pinna of the user's ear.

Also described herein are other embodiments that attach in or behind a user's ear to direct a magnetic field to the inner ear to improve blood flow and oxygen levels for treatment of one or all of tinnitus, sudden sensorineural hearing loss, and vertigo. Some of these embodiments comprise an outer shell, magnetic material disposed within the outer shell, and a sound tube passing through the magnetic material. The outer shell has an outer profile that is custom-molded to fit within portions of the user's ear. The sound tube has an outer opening that receives sound from outside the user's ear and an inner opening through which the sound passes into the user's ear canal.

In some embodiments, the outer shell comprises an in-canal portion and an in-concha portion. The in-canal portion is configured to be disposed within the user's ear canal, and the in-concha portion is configured to be disposed within the user's ear concha. These embodiments include a faceplate that is attached to the in-concha portion of the outer shell to contain the magnetic material disposed therein.

In some embodiments, the outer opening of the sound tube is disposed in the faceplate, and the inner opening of the sound tube is disposed in the in-canal portion of the outer shell.

In some embodiments, the magnetic material comprises neodymium magnetic spheres.

In some embodiments, the neodymium magnetic spheres are encased in a filler material within the outer shell.

In some embodiments, the filler material comprises a hardened acrylic resin.

In some embodiments, wherein the filler material comprises silicone.

Also described herein are embodiments that attach around a user's ear to direct a magnetic field to the inner ear of a user to improve blood flow and oxygen levels for treatment of one or all of tinnitus, sudden sensorineural hearing loss, and vertigo. Some of these embodiments comprise an outer shell having an outer profile configured to fit behind the pinna of the user's ear, and magnetic material disposed within the outer shell. In some of these embodiments, the outer shell comprises a loop configured to at least partially encircle the user's outer ear.

BRIEF DESCRIPTION OF THE DRAWINGS

Other embodiments of the invention will become apparent by reference to the detailed description in conjunction with the figures, wherein elements are not to scale so as to more clearly show the details, wherein like reference numbers indicate like elements throughout the several views, and wherein.

DETAILED DESCRIPTION

Embodiments described herein are directed to wearable structures, also referred to herein as magnetic ear therapy apparatuses, that are worn over the ear, in the ear canal, in the concha, behind the ear, around the ear, or in combinations thereof.

Figure 1:
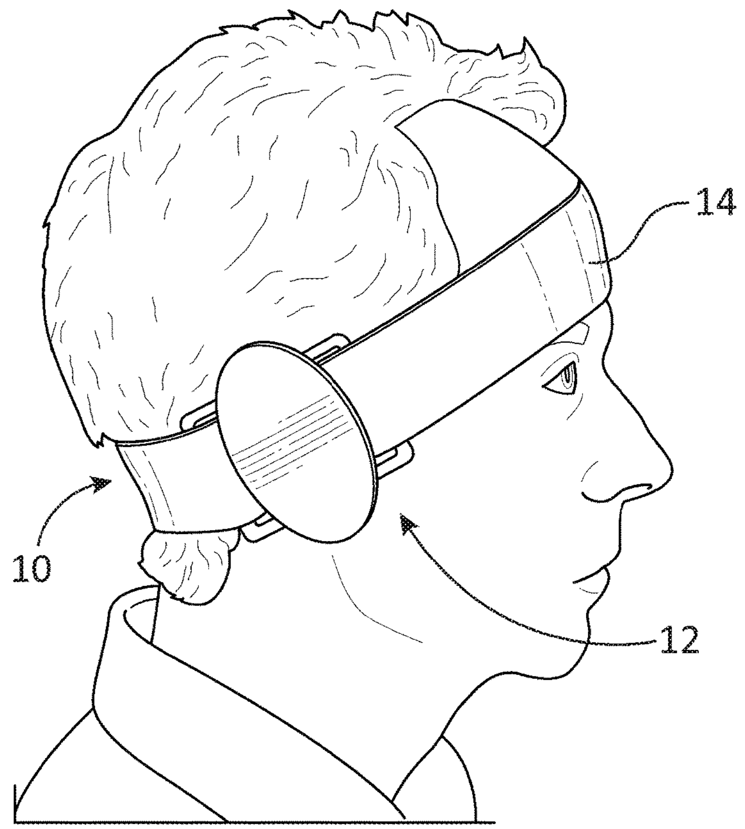
FIG. 1 depicts an over-the-ear (OTE) magnetic ear therapy apparatus according to a first embodiment of the invention.
Figure 2A:
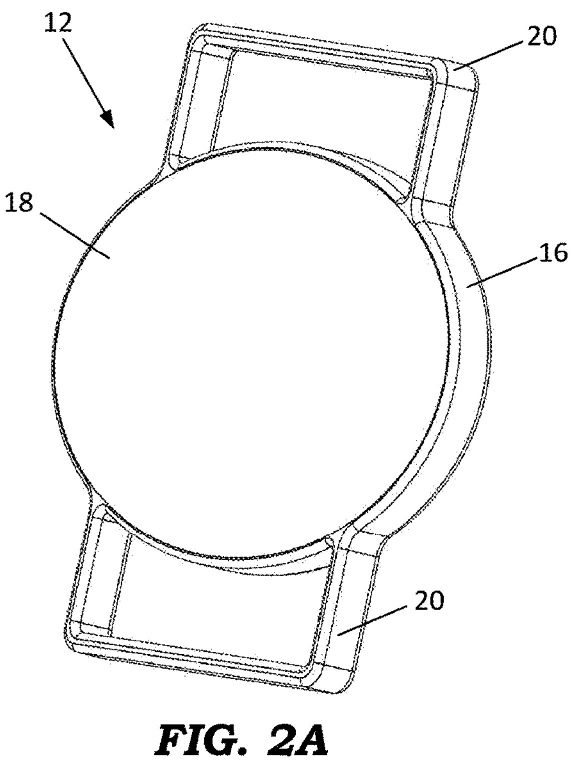
FIGS. 2A and 2B depict front and rear views, respectively, of a magnet housing assembly of the OTE magnetic ear therapy apparatus according to the first embodiment.
Figure 2B:
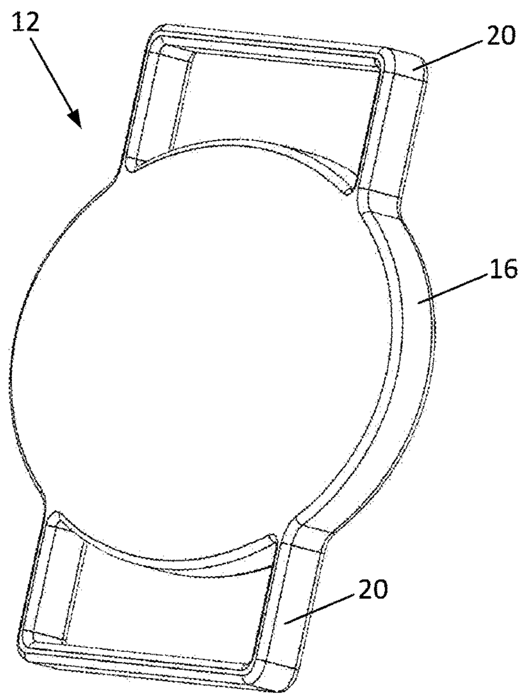

A first embodiment of a magnetic ear therapy apparatus 10 is depicted in FIGS. 1-6. As shown in FIG. 1, a pair of magnet housing assemblies 12 are attached to an elastic headband 14 worn around a user's head. The headband 14 and each housing assembly 12 are positioned such that the housing assemblies 12 are disposed over or adjacent the user's ears. Each magnet housing assembly 12 includes a base portion 16, a cover portion 18, lug portions 20 through which the headband 14 passes, and magnetic material 22 disposed between the base portion 16 and the cover portion 18. It will be appreciated that FIG. 1 shows one of the two housing assemblies 12, the other being disposed on the other side of the user's head.

Figure 3A:
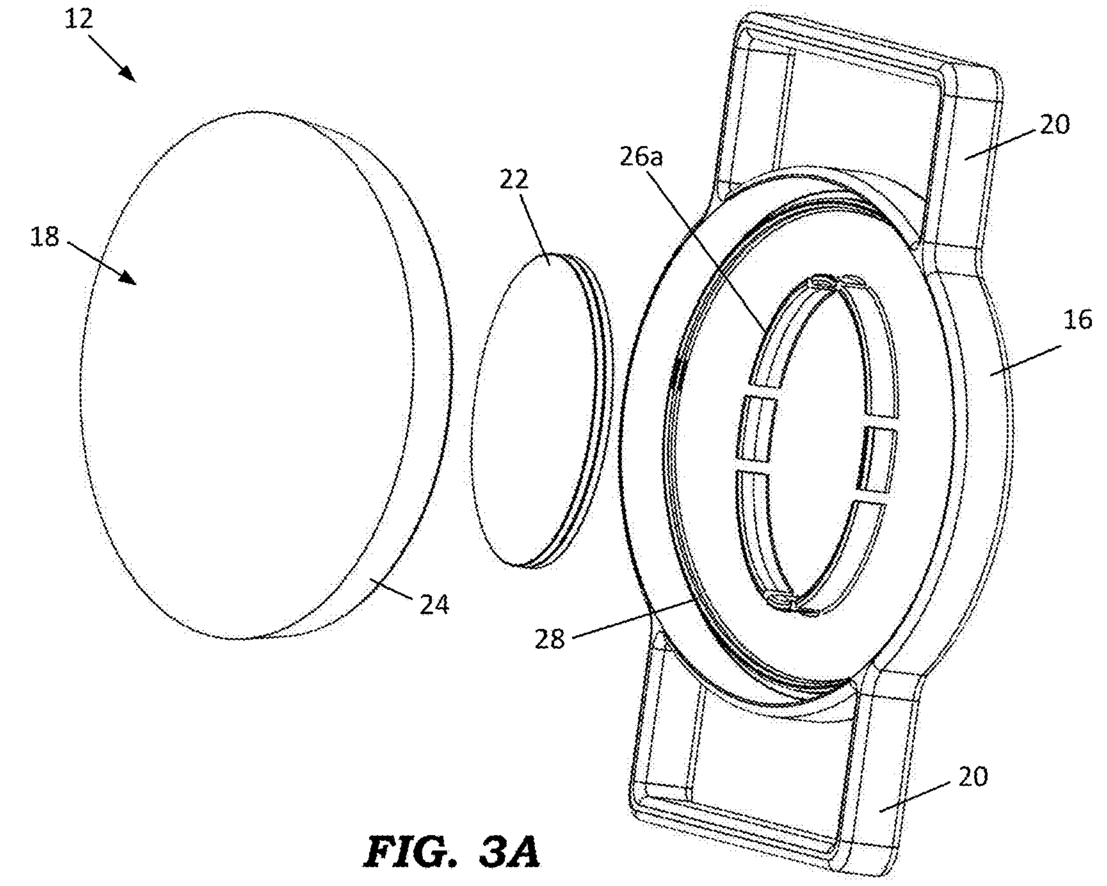
FIGS. 3A and 3B depict front and rear exploded views, respectively, of the magnet housing assembly according to the first embodiment.
Figure 3B:
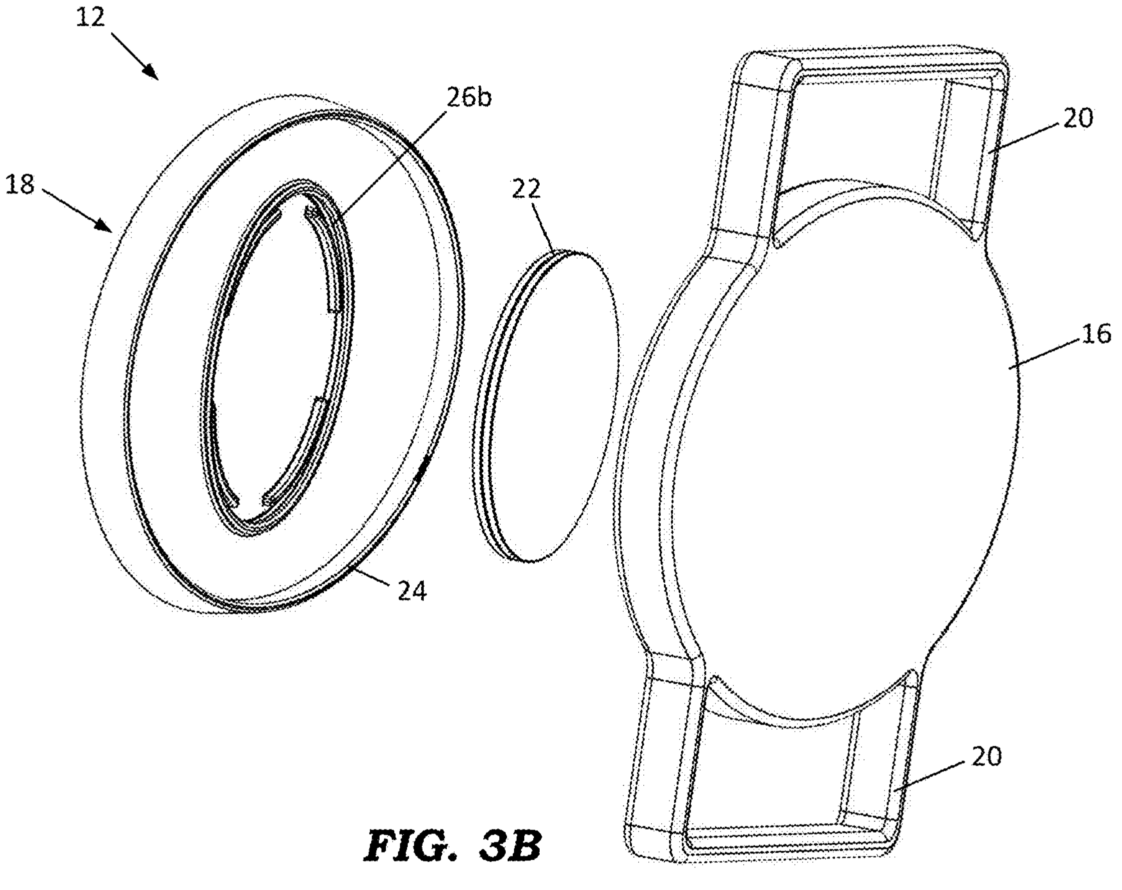
Figure 4B:
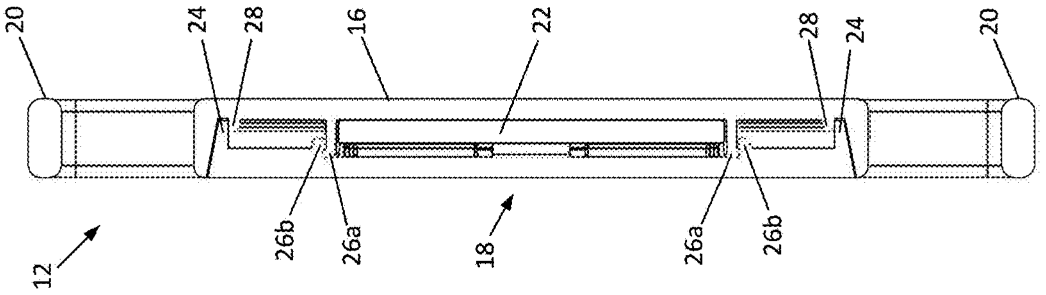
FIGS. 4A and 4B depict a front view and a cross section view, respectively, of the magnet housing assembly according to the first embodiment.
Figure 4A:
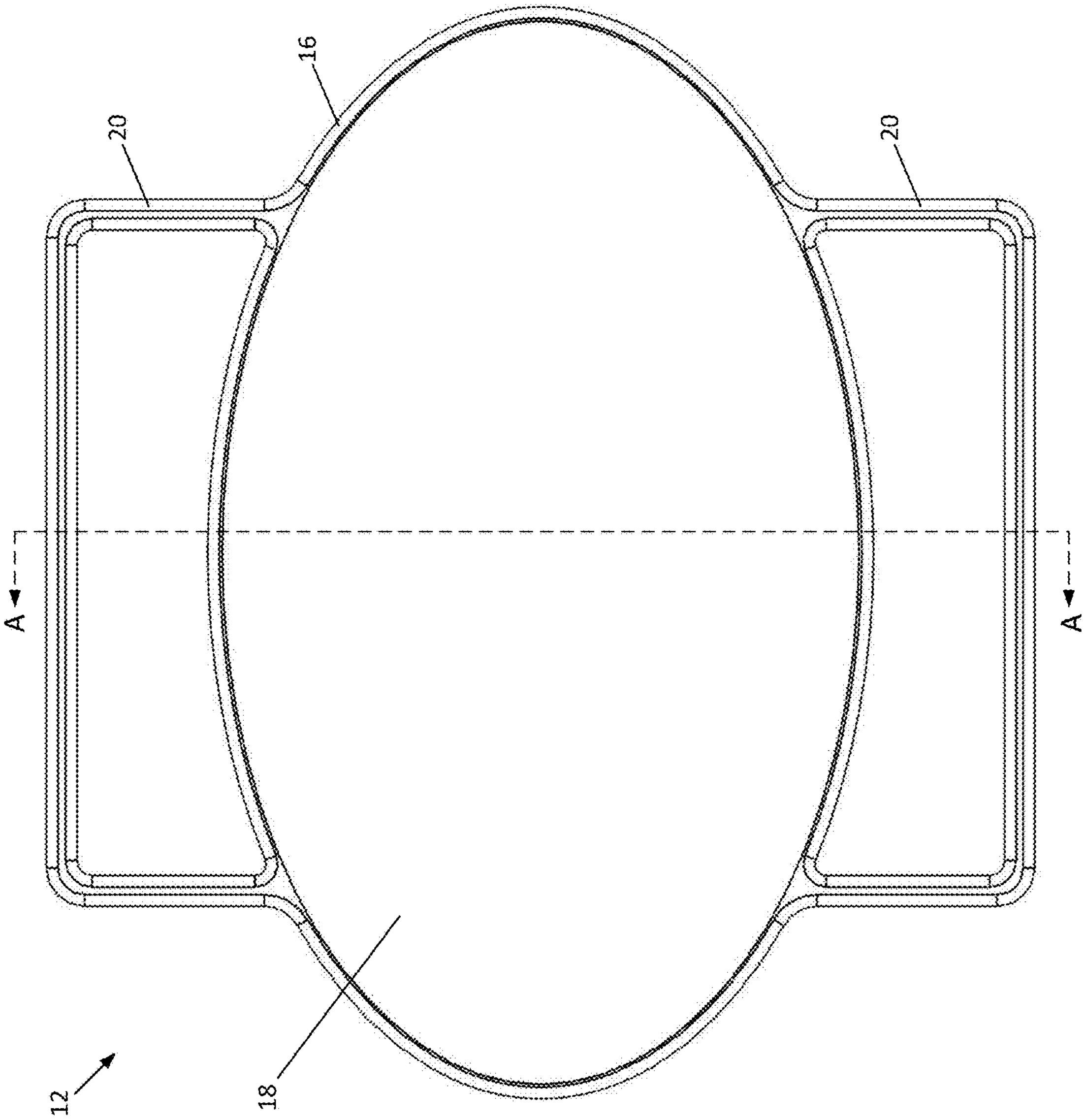
Figure 5:
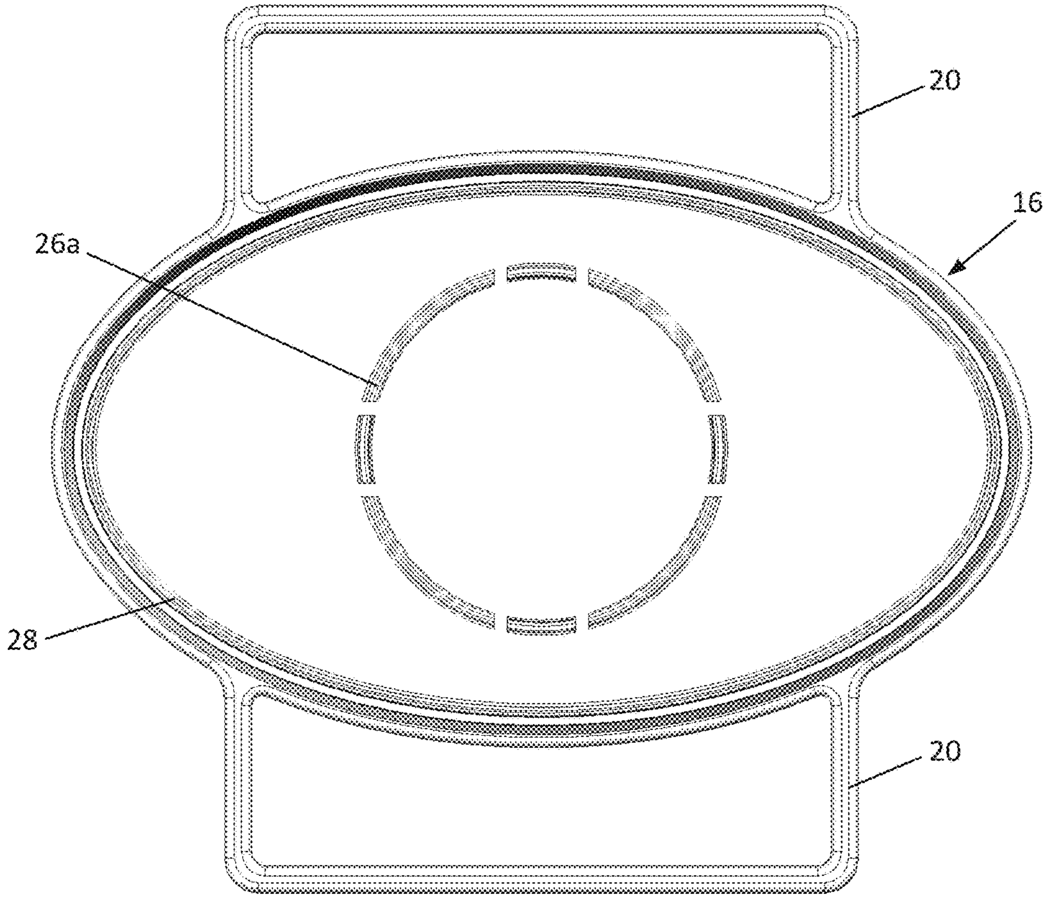
FIG. 5 depicts the inner surface of a base portion of the magnet housing assembly according to the first embodiment.
Figure 6:
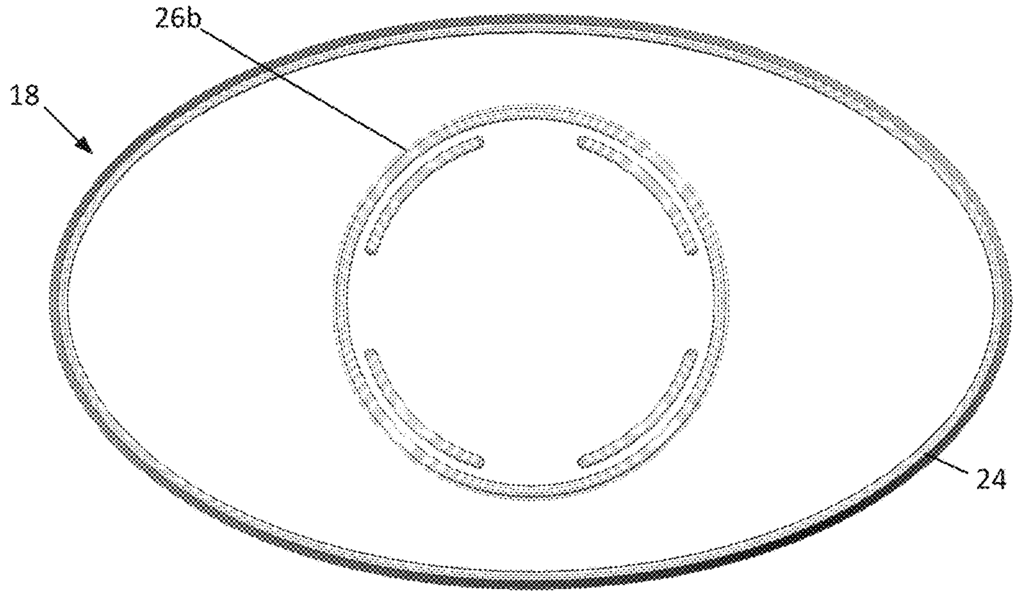
FIG. 6 depicts the inner surface of a cover portion of the magnet housing assembly according to the first embodiment.

In a preferred version of the first embodiment, the outer perimeter of the base portion 16 is oval-shaped and sized to substantially cover the pinna of the user's ear, with the lug portions 20 extending from the opposing wider sides of the base portion 16. It will be appreciated that the outer perimeter of the base portion 16 could have other shapes in other embodiments, such as rectangular or circular. As shown in FIGS. 3A, 4B and 5, central magnet cradle protrusions 26*a* and a perimeter protrusion 28 extend inwardly from the inside surface of the base portion 16. Preferably, the base portion 16, the lug portions 20, the central magnet cradle protrusions 26*a*, and the perimeter protrusion 28 are integrally formed as a single piece of molded plastic.

In the preferred embodiment, the cover portion 18 has an outer perimeter that is also oval-shaped and sized to match the outer perimeter of the base portion 16. As depicted in FIGS. 3A, 3B, 4B and 6, the cover portion 18 has an outwardly extending lip 24 configured to be received within a matching channel formed by the perimeter protrusion 28 along the inside edge of the base portion 16. The cover portion 18 also includes central magnet cradle protrusions 26*b* extending inwardly from its inside surface. Preferably, the cover portion 18, the lip 24 and the central magnet cradle protrusions 26*b* are integrally formed as a single piece of molded plastic.

In a preferred embodiment, the magnetic material 22 comprises one or more disc-shaped nickel-plated neodymium magnets, each having a diameter of 1.0 inch and thickness of 0.06 inch. One such magnet alone has a magnetic flux density of about 580 Gs. In the embodiment depicted in FIGS. 3A-3B, the magnetic material 22 includes two magnets having a combined magnetic flux density of about 1090 Gs. Three of the magnets combined have a magnetic flux density of about 1390 Gs. In various embodiments, one, two or more magnets may be provided depending on the type of treatment needed. It will be appreciated that other shapes and arrangements of magnets may be provided, depending on the type of treatment needed. In one embodiment, multiple magnets may be provided, and the user has the option to use one, two or more magnets to achieve the magnetic flux density that is most effective for treatment of the user's tinnitus, vertigo or SSHL. In these embodiments, the cover portion 18 is removable from the base portion 16 so that the user may have access to insert the desired number of magnets.

As depicted in FIG. 4B, the central magnet cradle protrusions 26*a* in the base portion 16 engage the central magnet cradle protrusions 26*b* in the cover portion 18 in a snap-fit arrangement such that the magnetic material 22 is sandwiched between the base portion 16 and the cover portion 18, and within the central magnet cradle protrusions 26*a* and 26*b*.

Figure 7:
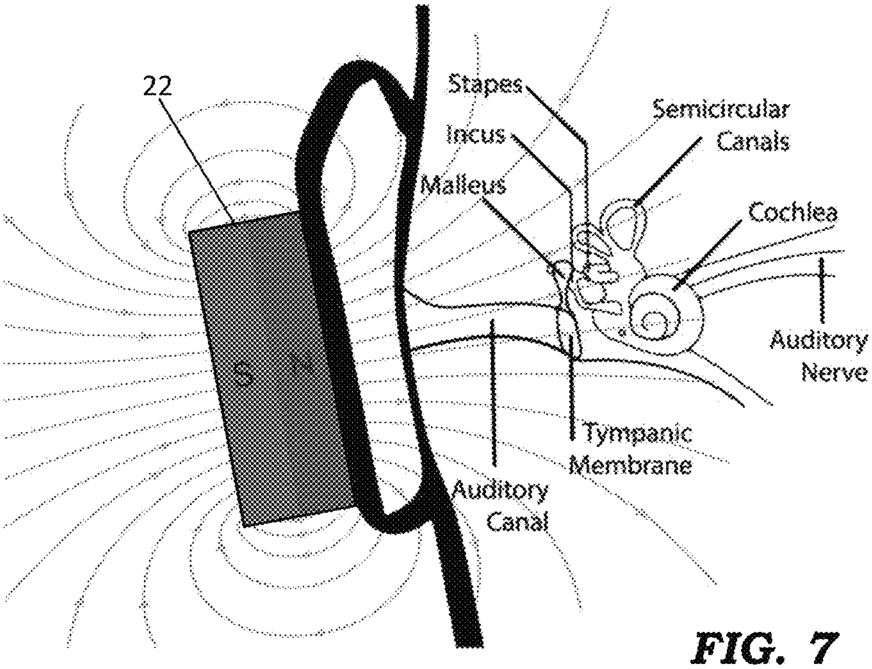
FIG. 7 depicts lines of magnetic flux generated by the magnet housing assembly according to the first embodiment.

FIG. 7 depicts an example of lines of magnetic field flux generated by the preferred embodiment of the magnetic ear therapy apparatus 10. As illustrated, the magnetic fields emanating from the north pole of the magnetic material 22 are directed to the structures of the user's inner ear to provide the benefits discussed herein, including improved blood flow and increased oxygen levels.

Figure 8A:
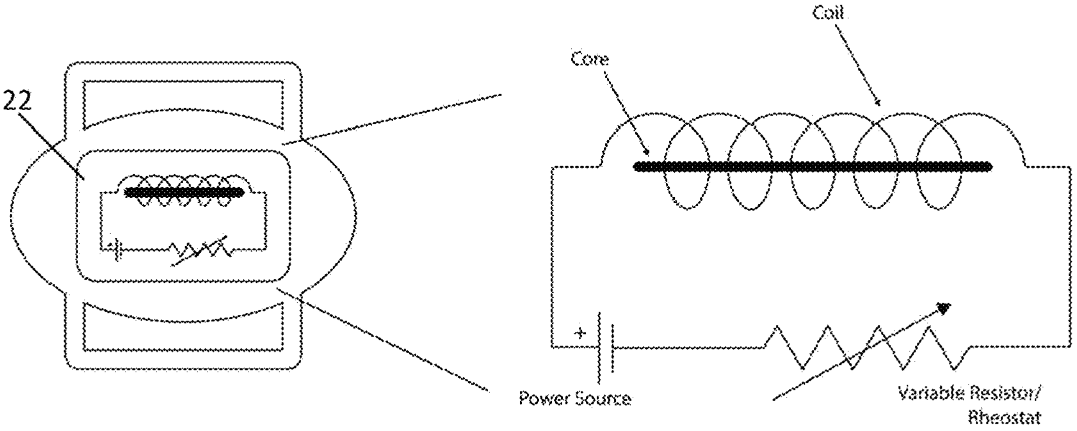
FIGS. 8A and 8B depict examples of electromagnetic circuits for generating magnetic fields according to the first embodiment.
Figure 8B:
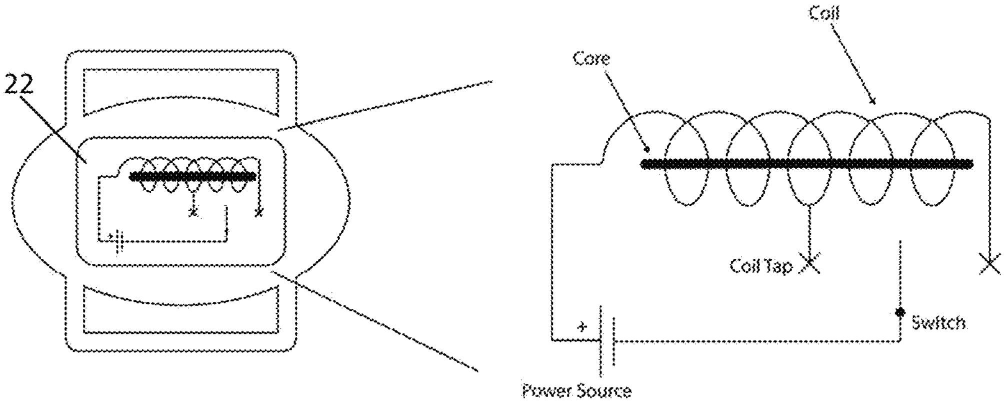

In some embodiments, the magnetic material 22 comprises an electromagnet for generating the magnetic field. In such embodiments, examples of which are depicted in FIGS. 8A and 8B, the user may adjust the magnetic flux density by controlling the voltage level provided to an electromagnetic coil. As illustrated, a switch or other control circuit may be provided to control a rheostat or to select a tap of the coil to control the voltage. Those skilled in the art will appreciate that digital control circuits could also be implemented for this purpose, and the control function may be provided wirelessly, such as via Bluetooth using an app on a mobile device such as a smart phone.

Figure 9:
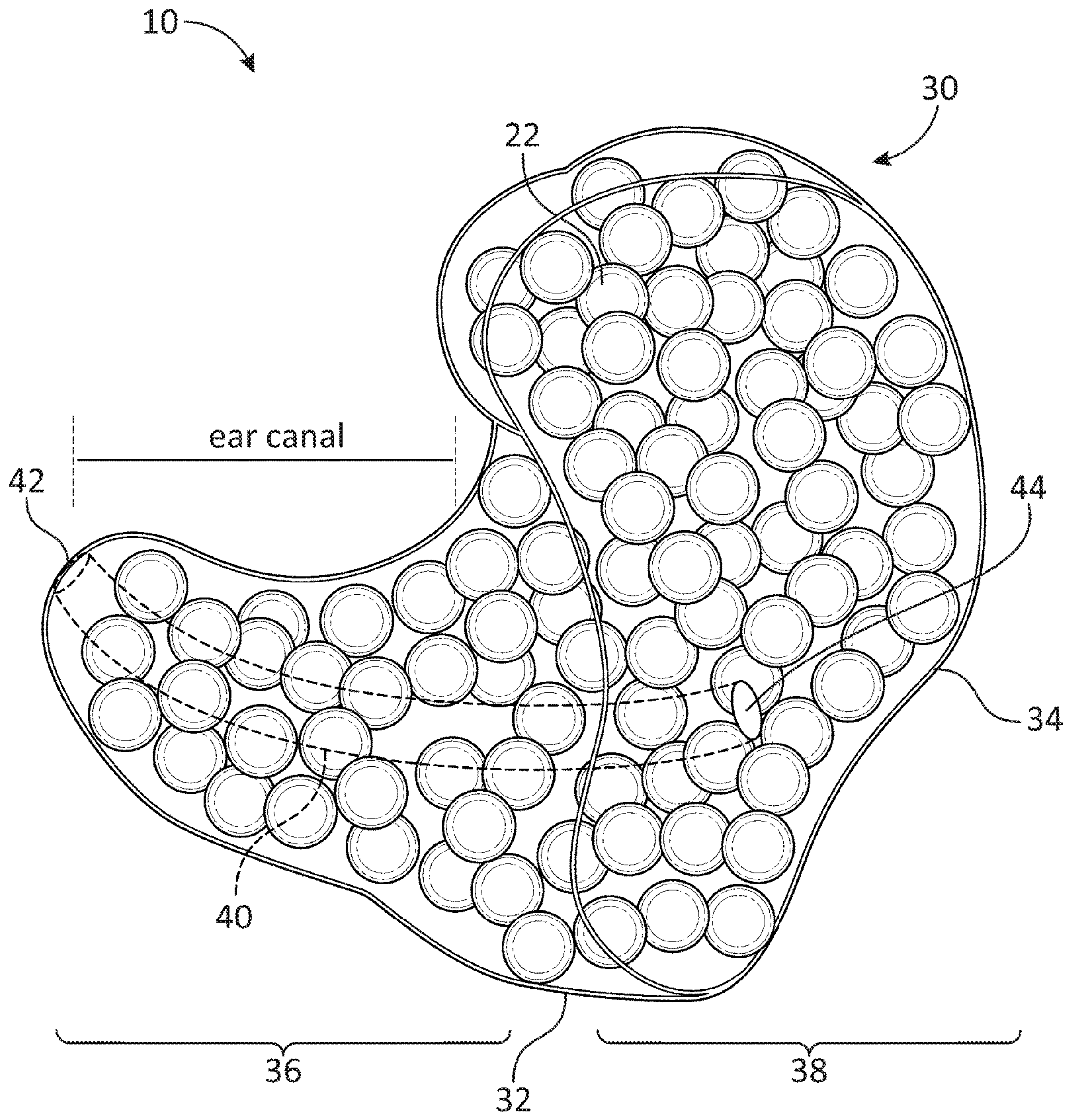
FIG. 9 depicts an in-the-ear (ITE) ear mold of a magnetic ear therapy apparatus according to a second embodiment of the invention.
Figure 10:
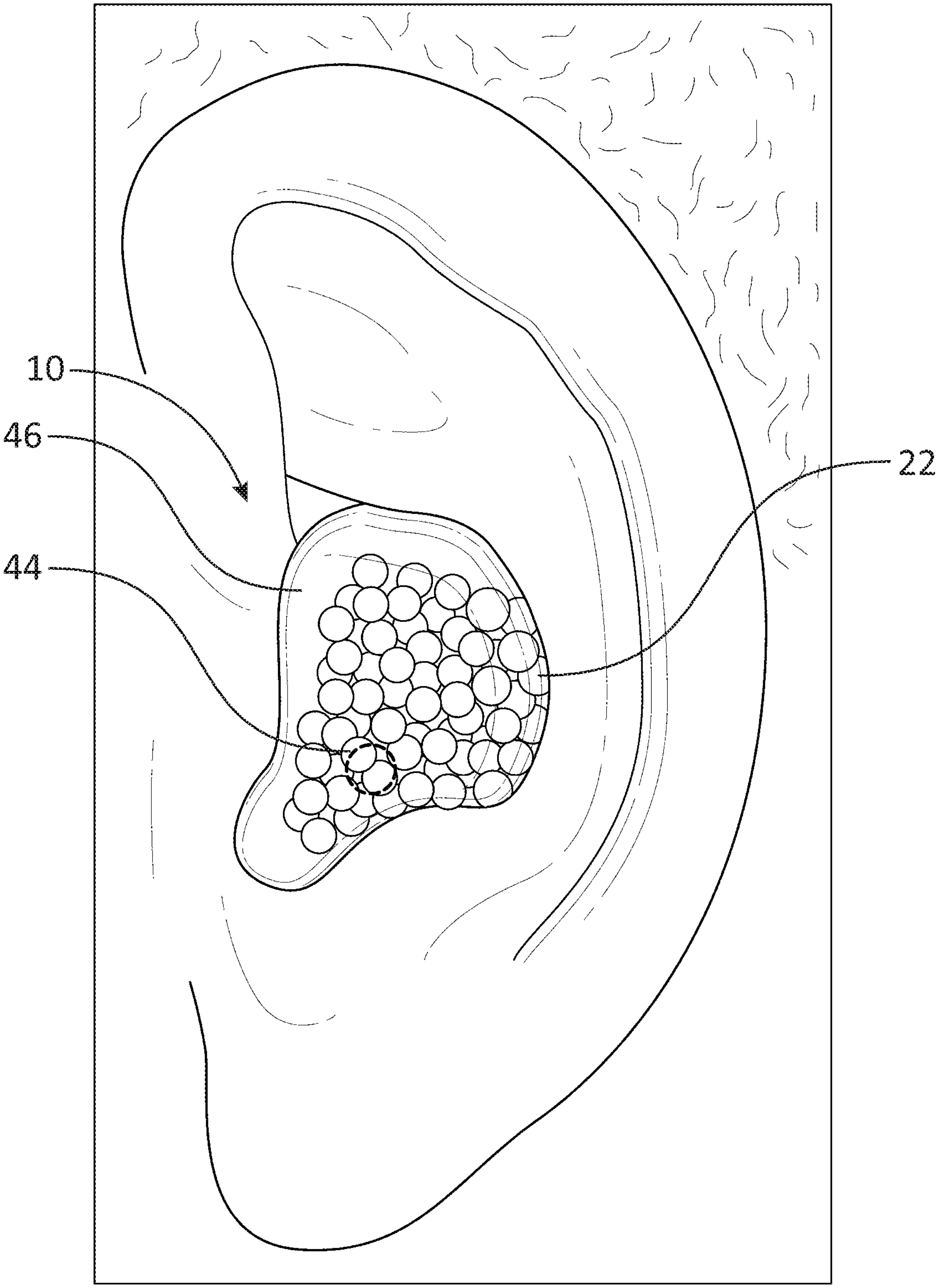
FIG. 10 depicts an ITE ear mold of a magnetic ear therapy apparatus according to the second embodiment disposed in a user's ear.
Figure 13A:
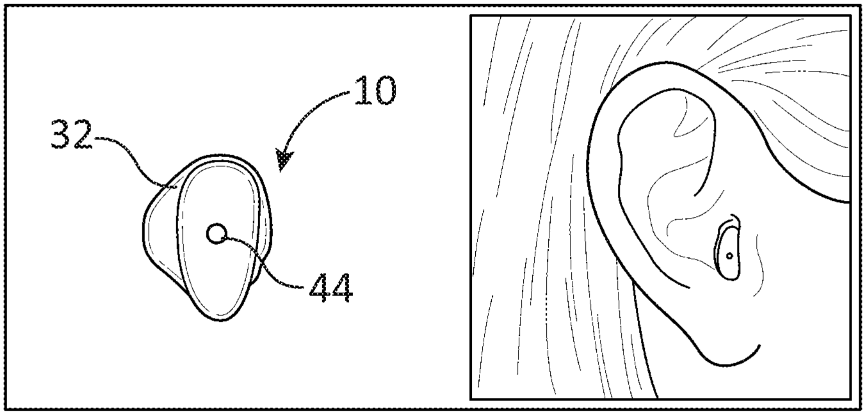
FIG. 13A depicts a completely-in-the-canal (CIC) ear mold of a magnetic ear therapy apparatus according to a fourth embodiment of the invention.
Figure 13B:
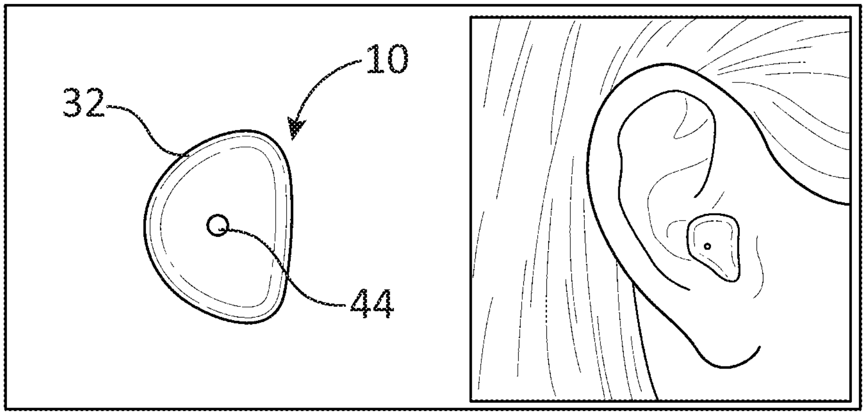
FIG. 13B depicts an in-the-canal (ITC) ear mold of a magnetic ear therapy apparatus according to a fifth embodiment of the invention.
Figure 13C:
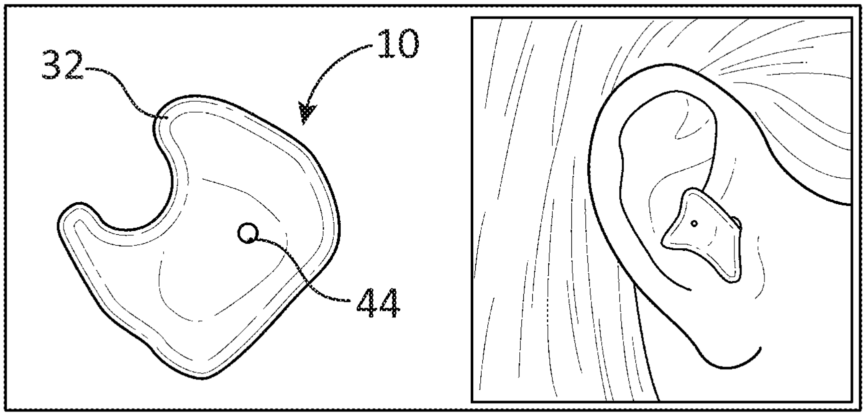
FIG. 13C depicts an ITE ear mold of a magnetic ear therapy apparatus according to the second embodiment of the invention.
Figure 13D:
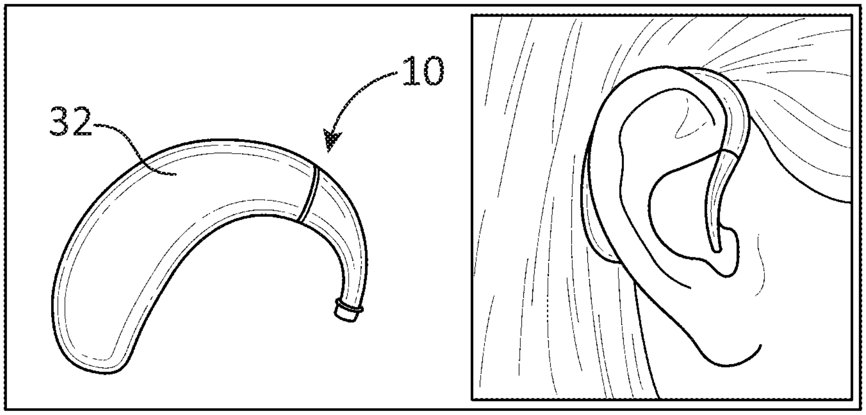
FIG. 13D depicts a behind-the-ear (BTE) housing assembly of a magnetic ear therapy apparatus according to a sixth embodiment of the invention.

In alternative embodiments, the magnetic ear therapy apparatus 10 comprises an ear mold 30 that encases magnetic materials 22, such as magnetic spheres, and that place the magnetic materials 22 in close proximity to blood vessels in the user's ear when worn as described herein. For example, a second embodiment of the magnetic ear therapy apparatus 10, as depicted in FIGS. 9, 10 and 13C, comprises an ITE ear mold 30 that includes a hollow outer shell 32 in which a magnetic material 22 is enclosed that is capped by a faceplate 34. The outer shell 32 includes an in-canal portion 36 that is disposed within the user's ear canal when worn, and an in-concha portion 38 disposed in the user's ear concha. In a preferred embodiment, the outer shell 32 is formed based on an impression made of the individual user's ear canal and concha, as may typically be done in the manufacturing of custom hearing aid housings. The impression is used to craft the custom-fit outer shell 32.

The magnetic material 22 may comprise magnetic spheres, such as neodymium spheres having a diameter of 3 mm. The spheres are preferably encased in a filler within the outer shell. The filler may be a hardened acrylic resin or a softer material such as silicone. In an alternative embodiment, the magnetic material 22 is a flowable ferromagnetic filling that can be magnetized after the outer shell 32 is filled.

Disposed within the outer shell 32 is a sound tube 40 having an inner opening 42 at the end of the in-canal portion 36 of the outer shell 32 and an outer opening 44 in the faceplate 34 that covers the in-concha portion 38 of the outer shell 32. The sound tube 40 allows sound to travel from outside the faceplate 34 through to the ear canal, so that the user's hearing is unimpeded. An alternative embodiment may include slits or channels on the outside surfaces of the outer shell 32 to allow sound to travel around the outer shell into the ear canal.

Figure 11:
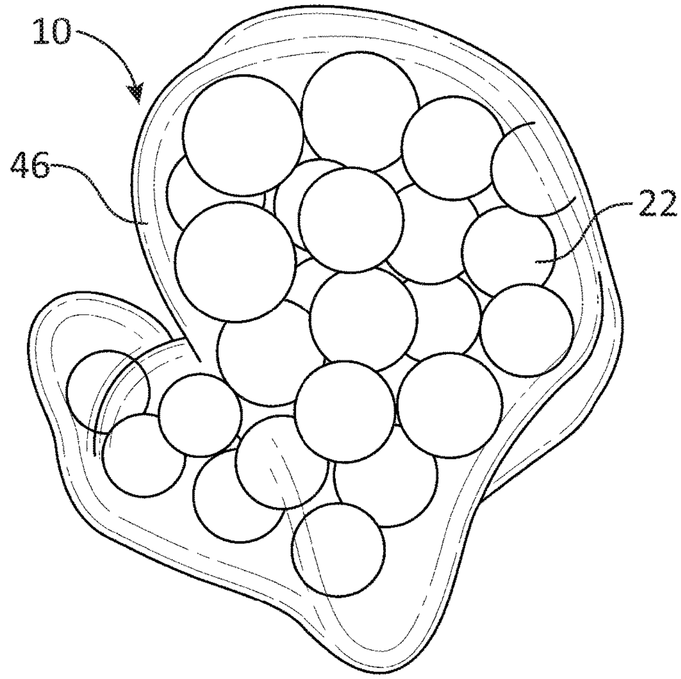
FIG. 11 depicts an ITE ear mold of a magnetic ear therapy apparatus without a sound tube according to a third embodiment of the invention.
Figure 12:
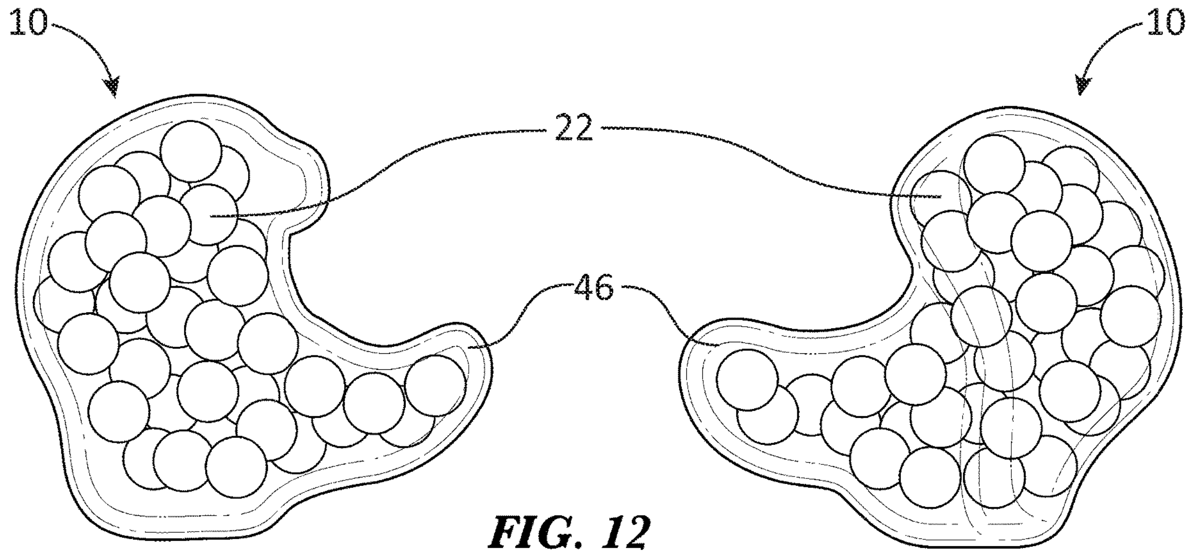
FIG. 12 depicts ITE ear molds of magnetic ear therapy apparatuses for left and right ears without a sound tube according to the third embodiment of the invention.

FIGS. 10, 11 and 12 depict ITE ear mold embodiments of the magnetic ear therapy apparatus 10 in which the magnetic material 22 (such as magnetic spheres) are embedded in acrylic resin 46. It will be noted that no sound tube is shown in the embodiments of FIGS. 11 and 12.

FIGS. 13A, 13B, 13C and 13D depict, respectively, a CIC embodiment of the magnetic ear therapy apparatus 10 having a pull-string for removal, an ITC embodiment, the ITE embodiment, and a BTE embodiment. Preferably, the BTE embodiment is attached by a custom earpiece that is molded to fit the shape of the user's outer ear.

Figure 14A:
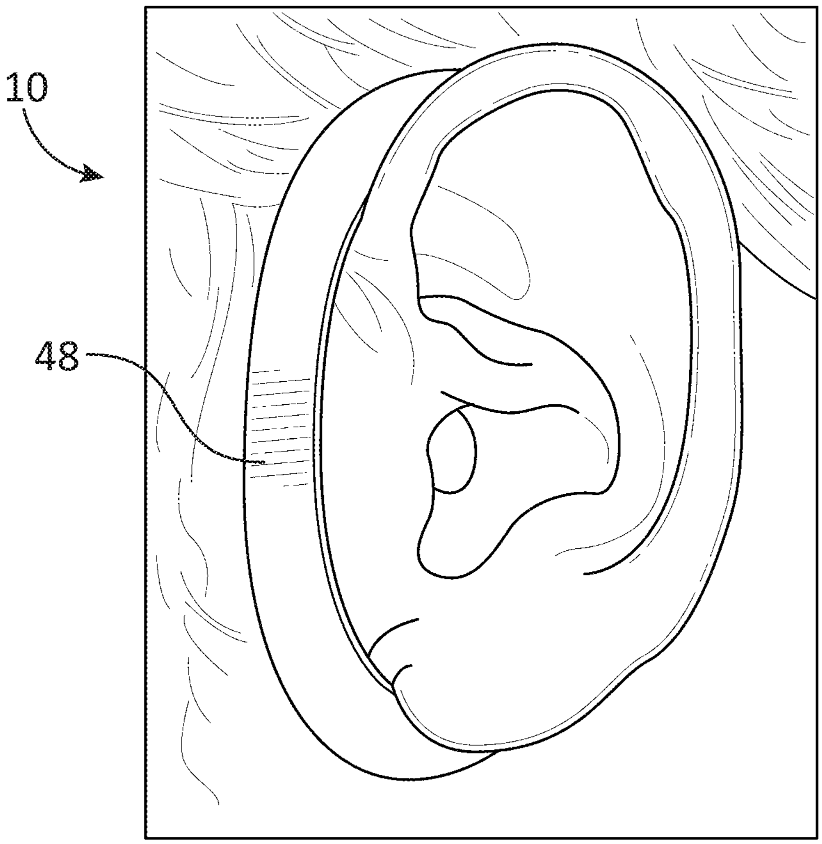
FIGS. 14A and 14B depict an around-the-ear housing assembly of a magnetic ear therapy apparatus according to a seventh embodiment of the invention.
Figure 14B:
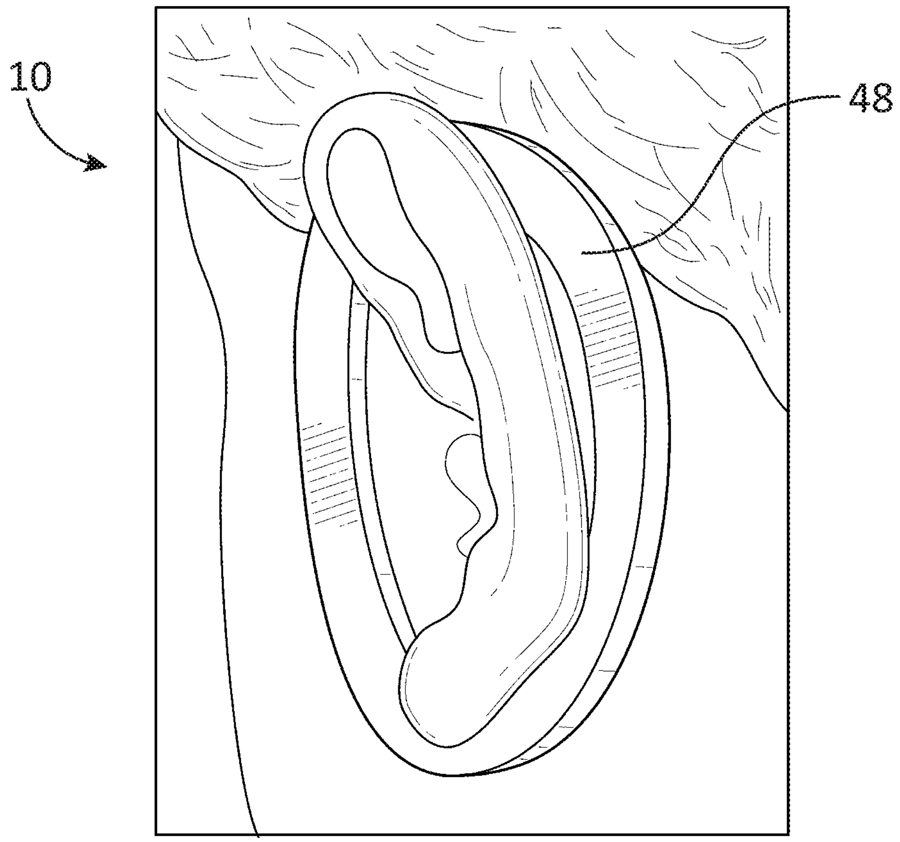

FIGS. 14A and 14B depict an around-the-ear housing assembly 48 in which magnetic material is encased that completely surrounds a user's ear. This version could be worn alone or in combination with the versions depicted in FIGS. 13A, 13B and 13C.

The foregoing description of preferred embodiments for this invention have been presented for purposes of illustration and description. They are not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. An apparatus for directing a magnetic field to an inner ear of a user to improve blood flow and oxygen levels for treatment of one or all of tinnitus, sudden sensorineural hearing loss, and vertigo, the apparatus comprising:

an outer shell having an outer profile that is custom-molded to fit one or more portions of an ear of the user, the outer shell comprising an in-canal portion configured to be disposed within the user's ear canal and an in-concha portion configured to be disposed within the user's ear concha;

magnetic material disposed within the in-canal portion and the in-concha portion of the outer shell, wherein the magnetic material comprises magnetic spheres;

a faceplate attached to the in-concha portion of the outer shell; and a sound tube disposed within the outer shell and passing through the magnetic material in one or both of the in-canal portion and in the in-concha portion of the outer shell, the sound tube having an outer opening disposed on the faceplate that receives sound from outside the ear of the user and an inner opening disposed on the in-canal portion through which the sound passes into the user's ear canal.

2. The apparatus of claim 1 wherein the magnetic spheres comprise neodymium magnetic spheres.

3. The apparatus of claim 2 wherein the neodymium magnetic spheres are encased in a filler material within the outer shell.

4. The apparatus of claim 3 wherein the filler material comprises a hardened acrylic resin.

5. The apparatus of claim 3 wherein the filler material comprises silicone.

* * * * *